United States Patent [19]

Shek

[11] Patent Number: 5,784,743
[45] Date of Patent: Jul. 28, 1998

[54] ELECTRIC TOOTHBRUSHES

[75] Inventor: Kwok Nam Shek, Tuen Mun, Hong Kong

[73] Assignee: Addway Engineering Limited, Hong Kong

[21] Appl. No.: 777,534

[22] Filed: Dec. 30, 1996

[51] Int. Cl.$^6$ ............................. A61C 17/34; A46B 13/02
[52] U.S. Cl. ................................. 15/22.1; 15/28
[58] Field of Search ............................. 15/21.1, 22.1, 15/28, 29

[56] References Cited

U.S. PATENT DOCUMENTS

| | | | |
|---|---|---|---|
| 5,416,942 | 5/1995 | Baldacci et al. | 15/22.1 |
| 5,577,285 | 11/1996 | Drossler | 15/22.1 |
| 5,625,916 | 5/1997 | McDougall | 15/22.1 |
| 5,652,990 | 8/1997 | Driesen et al. | 15/22.1 |

*Primary Examiner*—Terrence Till
*Attorney, Agent, or Firm*—Miller, Sisson, Chapman & Nash, P.C.

[57] ABSTRACT

An electric toothbrush has a drive shaft with an off-set finger. A pivotably supported wobble plate has a fork at one end and an arcuate drive gear at another end. The drive gear meshes with a gear rotatably fixed to a brush holder so that in use the brush holder is caused to oscillate. The arrangement provides more flexibility in design and in particular enables the maximum arc of oscillation to be significantly increased over similar prior art toothbrushes.

6 Claims, 1 Drawing Sheet

ELECTRIC TOOTHBRUSHES

BACKGROUND OF THE INVENTION

1. Field of the Invention

The invention relates to electric toothbrushes.

2. Description of Prior Art

An electric toothbrush has been described in which rotary motion is changed to oscillating circular motion. A drive shaft is used that is cranked at one end and engages a slot in a brush holder. As the drive shaft is continuously rotated by an electric motor, the cranked end engages the slot and caused the brush holder to oscillate. Due to certain overall maximum desirable dimensions for the brush holder, it is especially not convenient to oscillate the brush holder normally through an arc of more than about 90°. It may also be relatively difficulty to choose or change to different arcs of oscillation within the operable range.

SUMMARY OF THE INVENTION

It is an object of the invention to overcome or reduce one or both of these problems.

According to the invention there is provided an electric toothbrush having a handle, a brush head and a shank having a central longitudinal axis extending between the handle and the brush head, a drive shaft extending along the central axis from a motor in the handle to a remote end thereof and having a finger off-set from the central axis at the remote end, a wobble plate pivotably mounted on the central axis having a first end and a second end, a fork at the first end of the wobble plate that embraces the finger and an arcuate contact drive surface at the second end, a brush holder pivotably mounted by a shaft on the central axis to the brush head, and a circular contact surface rotatable with the shaft that engages the arcuate contact surface such that when the drive shaft is rotated by the motor continuously in one direction the brush holder is rotated backwards and forwards.

The arcuate contact drive surface and the circular contact surface are preferably each formed with gearing that mesh with one another.

The arcuate contact drive surface may be arranged to mesh with the circular contact surface in a region beyond the axis of the brush holder from the shank.

The wobble plate is preferably integrally formed by molding.

The finger may be mounted in one side of a circular boss fixed to a remote end of the drive shaft.

A bearing is preferably provided adjacent the remote end that is mounted to the shank to centralize the drive shaft on the central axis.

BRIEF DESCRIPTION OF THE DRAWINGS

An electric toothbrush according to the invention will now be described by way of example with reference to the accompanying drawings in which.

DESCRIPTION OF THE PREFERRED EMBODIMENT

Figure 1:
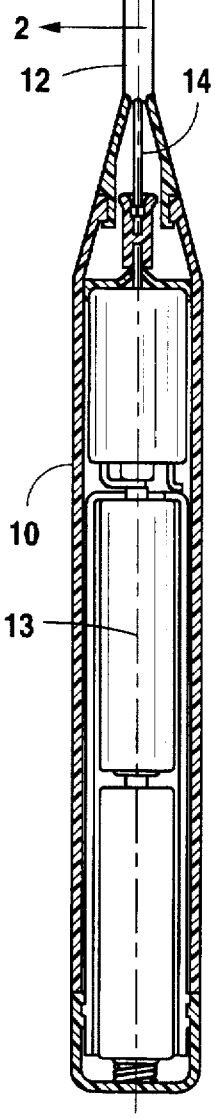
FIG. 1 is a part-sectioned underplan view of the toothbrush.

Referring to the drawings, in FIG. 1 the toothbrush comprises a handle 10, a brush head 11 and shank 12 having a central longitudinal axis 13.

Figure 2:
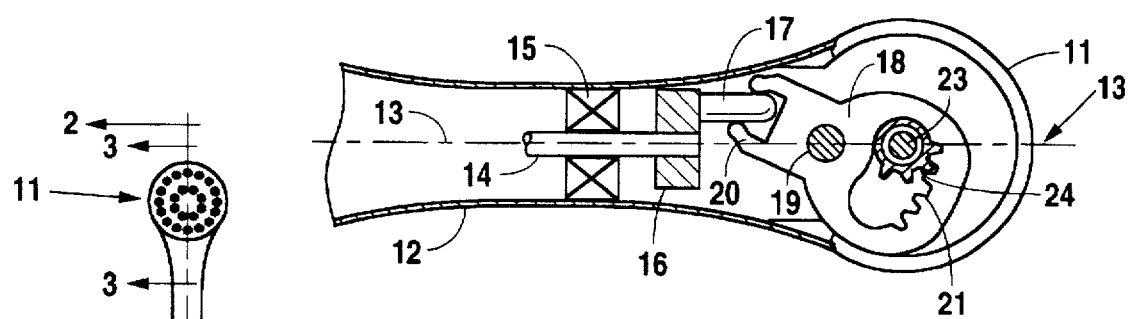
FIG. 2 is a bottom plan sectional views of part of the toothbrush.
Figure 3:
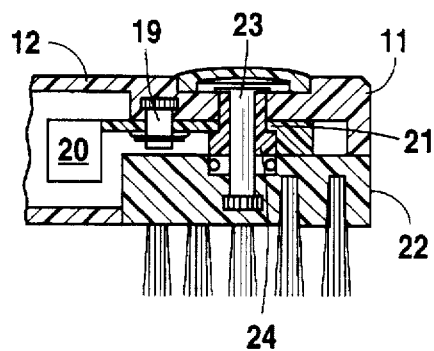
FIG. 3 is a side sectional elevation of part of the toothbrush.
Figure 4:
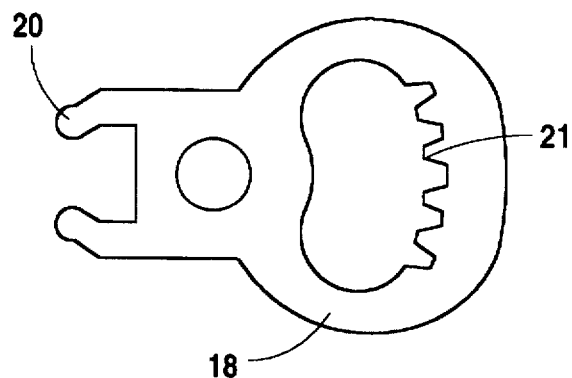
FIG. 4 is an enlarged plan view of a wobble plate for the toothbrush.

In FIGS. 2, 3 and 4, a drive shaft 14 is mounted to rotate about the central axis 13 and is held in position at a remote end by a bearing 15. A boss 16 mounted on the remote end of the shaft 14 is provided with a finger 17 that is off-set from the central axis 13. A wobble plate 18 is pivotably mounted on a short shaft 19, on the axis 13, fixed to the brush head 11. The wobble plate 18 has a first end integrally formed as a fork 20 that embraces the finger 17 and a second end which carries an arcuate gear 21. A brush holder 22 is pivotably mounted on a pivot shaft 23, also on the central axis 13, fixed to the brush head 11. The shaft 23 is provided with a gear 24, rotatably fixed to the shaft, that meshes with the arcuate gear 21.

When the drive shaft 14 is rotated continuously in one direction, the brush holder 22 is caused to rotate backwards and forwards, or oscillate, about its central pivot axis. In general terms, the relative position of the shaft 19 and the shaft 23 can be varied significantly and the gearing between the gears 21 and 24 altered to produce various arcs of oscillation that may be desired. The arcs of oscillation can range well above 120° for example.

It will also be noted that the gears 21 and 24 may be positioned at either side of the axis of the shaft 23 to increase the possible oscillating arc ranges further. Also, although gears are usually preferable, the drive connection between the wobble plate and the brush holder may comprise relatively smooth contact or rubbing surfaces. This can enable the brush holder to be manually rotated relate to the wobble plate if bristles of the brush become unevenly worn so that oscillations thereafter use a different part of the contact surface of the brush holder. Such manual rotation may also be helpful it the first part of the brush holder contact surface starts slipping due to wear, for example.

The wobble plate 18 (seen best in FIG. 4) is an integrally formed molded plastic part. The drive shaft 14 may also be integrally formed in plastic material or formed of steel wire where the finger 17 is formed by cranking the remote end of the wire.

We claim:

1. An electric toothbrush having a handle, a brush head and a shank having a central longitudinal axis extending between the handle and the brush head, a drive shaft extending along the central axis from a motor in the handle to a remote end thereof and said drive shaft having a finger off-set from the central axis at the remote end, a wobble plate pivotably mounted on the central axis having a first end and a second end, a fork at the first end of the wobble plate that embraces the finger and an arcuate contact drive surface at the second end, a brush holder pivotably mounted by a shaft on the central axis to the brush head, and a circular contact surface rotatable with the shaft that engages the arcuate contact surface such that when the drive shaft is rotated by the motor continuously in one direction the brush holder is rotated backwards and forwards.

2. An electric toothbrush according to claim 1, in which the arcuate contact drive surface and the circular contact surface are each formed with gearing that mesh with one another.

3. An electric toothbrush according to claim 2, in which the arcuate contact drive surface is arranged to mesh with the circular contact surface in a region beyond the axis of the brush holder from the shank.

4. An electric toothbrush according to claim 3, in which the wobble plate is integrally formed by molding.

5. An electric toothbrush according to claim 1, in which the finger is mounted in one side of a circular boss fixed to a remote end of the drive shaft.

6. An electric toothbrush according to claim 1, including a bearing adjacent said remote end mounted to the shank to centralize the drive shaft on the central axis.

* * * * *